United States Patent [19]
Geiger

[11] Patent Number: 5,133,184
[45] Date of Patent: Jul. 28, 1992

[54] METHOD AND APPARATUS FOR MONITORING THE CONVERSION RATIO OF A CATALYTIC CONVERTER

[75] Inventor: Istvan Geiger, Braunschweig, Fed. Rep. of Germany

[73] Assignee: Volkswagen AG, Fed. Rep. of Germany

[21] Appl. No.: 654,062

[22] Filed: Feb. 11, 1991

[30] Foreign Application Priority Data

Feb. 10, 1990 [DE] Fed. Rep. of Germany ....... 4004066

[51] Int. Cl.$^5$ ................................. F01N 3/20
[52] U.S. Cl. ............................. 60/274; 60/277; 60/285; 60/286
[58] Field of Search ................ 60/274, 277, 286, 285

[56] References Cited

U.S. PATENT DOCUMENTS 4,953,351  9/1990  Motz ..................................... 60/276

FOREIGN PATENT DOCUMENTS 232106  9/1989  Japan ..................................... 60/277

Primary Examiner—Douglas Hart
Attorney, Agent, or Firm—Brumbaugh, Graves, Donohue & Raymond

[57] ABSTRACT

To provide assured monitoring of the conversion ratio of an exhaust gas catalytic converter in the exhaust system of an internal combustion engine of a motor vehicle, at least one ignition suppression is generated and a preset quantity of fuel-air mixture is supplied during a deceleration phase of the engine and the difference in the temperatures at locations downstream and upstream with respect to the flow of exhaust gas through the catalytic converter is detected and evaluated.

13 Claims, 2 Drawing Sheets

METHOD AND APPARATUS FOR MONITORING THE CONVERSION RATIO OF A CATALYTIC CONVERTER

BACKGROUND OF THE INVENTION

This invention relates to arrangements for monitoring the operation of catalytic converters.

It is known to use catalytic converters for the conversion of harmful components in the exhaust gases of internal combustion engines, in particular, those used for operating motor vehicles. These catalysts include those which convert hydrocarbons and carbon monoxide contained in the exhaust gases into materials which are not injurious to health. The operating life of such catalysts is limited because they are exposed to great stresses in operation, in particular, high temperatures as well s jarring during the operation of the vehicle. This means that after a period of time, which depends on the mode of operation of the associated internal combustion engine, the conversion ratio of the catalyst is reduced to levels which require replacement of the catalytic converter.

For this reason, methods for monitoring of the conversion ratio of a catalytic converter are known, as described, for example, in German Patent No. 26 43 739. According to the patent, the temperature at various locations in the housing of a catalytic converter, such as upstream and downstream from the converter, is measured during operation of the converter. By a comparison of the measured temperature values, the conversion ratio is determined and a warning signal is generated in the event of a critical reduction in the conversion ratio. Aside from the fact that these known methods are only carried out at the end of the warm-up phase of the catalytic converter after its starting temperature has been reached, the known methods do not take into account the fact that the measured temperatures are dependent not only on the state of the catalytic converter, but especially on the load on the internal combustion engine at the time of measurement. Internal combustion engines for motor vehicles in particular have a large variation in load and in revolutions per minute so that the quantity of exhaust gases (and thus the flow velocity through the catalytic converter) and the exhaust gas temperature are subject to large variations. Therefore, such known methods, which are carried out in the course of normal operation of the internal combustion engine under varying load, do not provide an accurate indication of the specific degree of activity of the catalytic converter.

SUMMARY OF THE INVENTION

Accordingly, it is an object of the present invention to provide an arrangement for monitoring the operation of a catalytic converter which overcomes the above-mentioned disadvantages of the prior art.

Another object of the invention is to provide a method and an apparatus for monitoring the conversion ratio of a catalytic converter which provides accurate and reproducible results, even when the internal combustion engine is operated with greatly varying loads.

These and other objects of the invention are attained by causing at least one ignition suppression during deceleration operation of a spark-ignited internal combustion engine so as to supply a defined quantity of unburned fuel-air mixture to the catalytic converter, and comparing temperature values at the catalytic converter during conversion of the mixture.

The invention also provides an advantageous way to generate signals for monitoring the conversion ratio of the catalytic converter during the operation of an internal combustion engine, in particular, during operation of a motor vehicle. During deceleration operation of the engine there are defined conditions with respect to the temperatures in the vicinity of the catalytic converter caused by at least one ignition suppression and by the supply of a defined quantity of fuel-air mixture to the engine, which temperatures are measured in accordance with the invention.

Although the method of the invention only monitors those reactions producing a positive heat output, i.e., oxidation of hydrocarbons and carbon monoxide, the results obtained can at normal aging of the catalytic converter also be used to draw conclusions regarding changes in the reducing effects on nitrogen oxide and nitrogen.

In this connection, it is possible to provide a control device by which, for example, one of the engine deceleration conditions is used for carrying out the method after the startup of the internal combustion engine. However, it is also possible to carry out the method in such a way that monitoring of the catalytic converter is performed at regular period intervals during operation of the engine when deceleration occurs.

Whenever the term "monitor signal" is used herein, it is intended to include any type of signal generation, not only a warning signal, but also, for example, a quantitative signal numerically indicating the degree of conversion. Such monitoring signals can be transmitted to the operator of the vehicle, but they can also be utilized for the transmission of some type of control action for engine operation.

BRIEF DESCRIPTION OF THE DRAWINGS

Further objects and advantages of the invention will be apparent from a reading of the following description is conjunction with the accompanying drawings in which.

DESCRIPTION OF PREFERRED EMBODIMENTS

Figure 1:
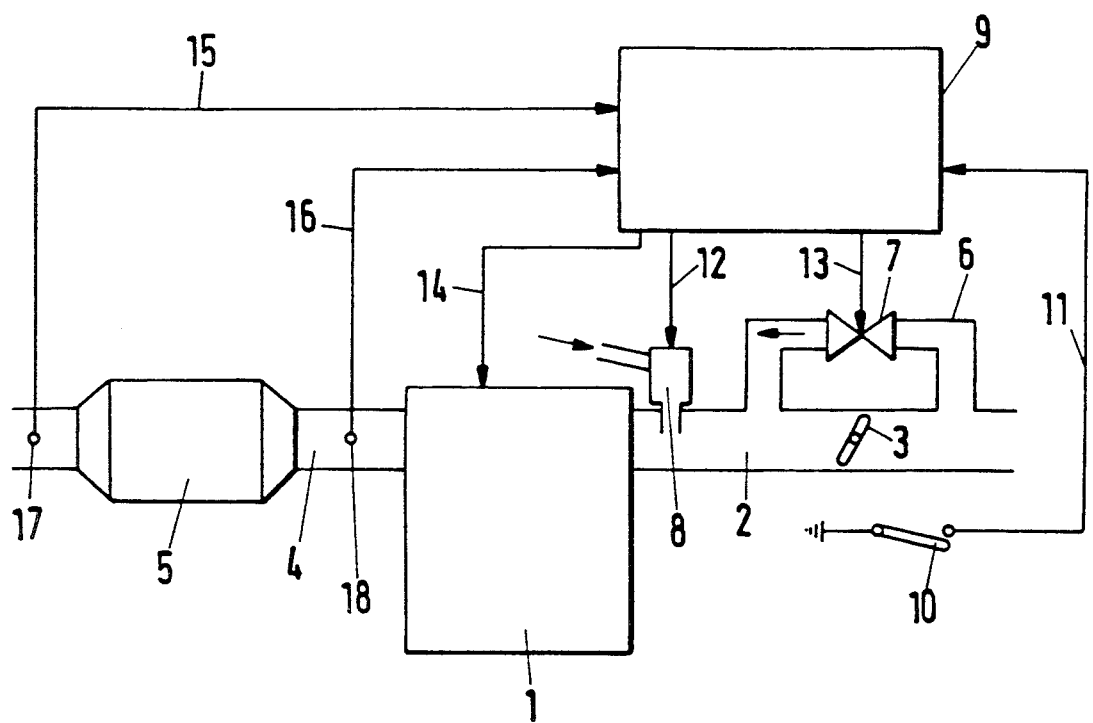
FIG. 1 is a schematic block diagram illustrating a representative arrangement for monitoring the conversion ratio of a catalytic converter in accordance with one embodiment of the invention.

In the typical embodiment of the invention shown in FIG. 1, an internal combustion engine 1 has an intake manifold 2 with a throttle flap 3, representing the engine output control element, and an exhaust system 4 having a catalytic converter 5 of known structure, which therefore need to be described in detail. Assuming that the internal combustion engine 1, which has spark ignition, is the motive force for a motor vehicle, the throttle flap 3 is responsive to the position of a gas pedal actuated by the driver. In FIG. 1, the throttle flap 3 is shown in its closed position which it assumes during idling, i.e., low engine rpm, and while carrying out conversion ratio determinations in accordance with the invention during deceleration, i.e., at rpm higher than during engine idle operation. Accordingly, during idling, the air flows through a bypass 6 in which a valve 7 for controlling the amount of air for idling is located. When conversion ratio determinations are made during deceleration, the flow crosssection of the valve 7 and the amount of fuel delivered through an injector nozzle 8 are set by a control unit 9. To characterize the deceleration operation, a throttle flap switch 10 is used together with a rpm siganl. The switch 10 is also closed during ratio determinations during deceleration with the throttle flap 3 closed and the gas pedal not actuated and supplies an appropriate activation signal to the control unit 9 through a line 11. As a result, the control unit 9 supplies control signals through two control lines 12 and 13 to control the operation of the devices 7 and 8 so as to carry out the method of the invention and also supplies a control signal through a control line 14 to cause at least one ignition suppression, i.e., spark failure.

Electrical signals indicating the respective temperature values at the locations of two temperature sensors 17 and 18 are supplied to the control unit 9 through corresponding lines 15 and 16. The temperature sensors 17 and 18 are located downstream and upstream, respectively, from the catalystic converter 5 in the direction of flow of the exhaust gases through the converter. Because a defined quantity of unburned fuel-air mixture supplied by control of the devices 7 and 8 reaches the catalytic converter 5 as a result of an ignition suppression, a chemical reaction takes place in the catalytic converter so that, if the catalytic converter is operating properly, the difference between the temperature values measured by the sensors 17 and 18 is relatively large and provides an unequivocal signal representing the conversion ratio of the converter.

Subtraction of the signals from the lines 15 and 16 takes place in the control unit 9, which is also designed for storing the difference signals which indicate the conversion ratio. Storage of these difference signals is important for the determination of the approximate point in time of a decrease of the conversion ratio. The control unit 9 can be programmed in such a way that the method described above is carried out during one of the first deceleration operations after each startup of the internal combustion engine 1, but only at a time after the catalytic converter 5 has reached its starting temperature, even when it has aged. Alternatively, the control unit 9 can be programmed in such a way that, after the passage of a given time interval following a conversion ratio determination, it waits for a deceleration condition of the internal combustion engine to occur and reinitiates the procedure at that time.

Figure 2:
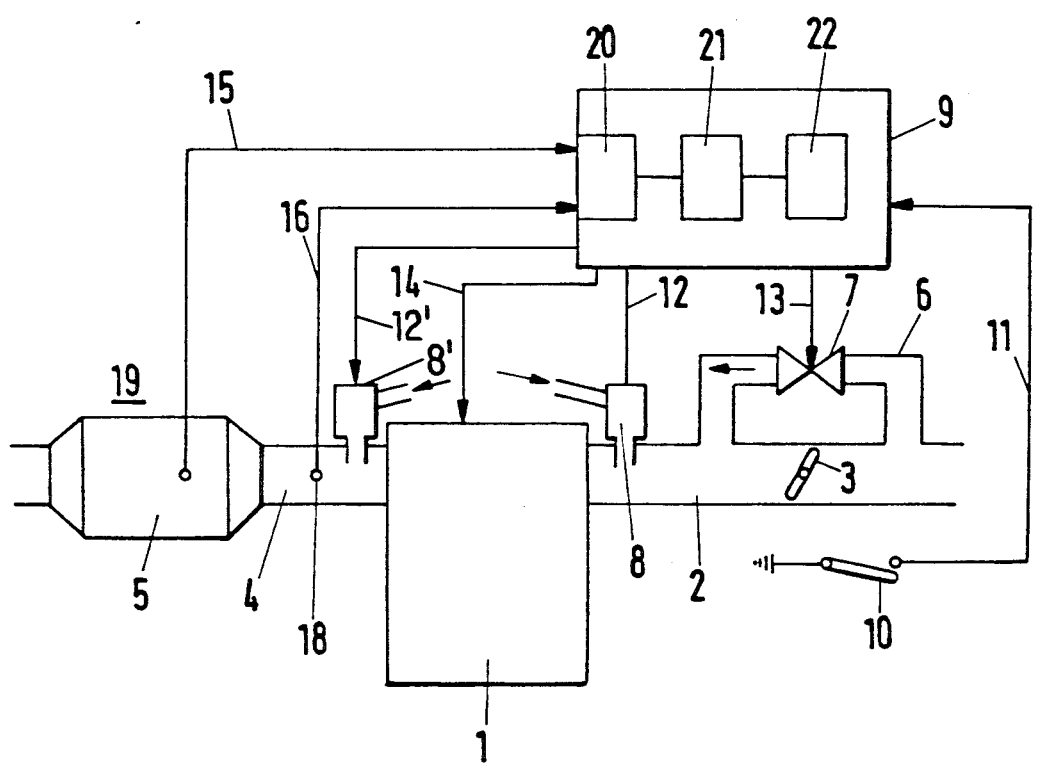
FIG. 2 is a schematic block diagram similar to FIG. 1 showing another embodiment of the invention.

In the alternative embodiment shown in FIG. 2, the parts which are also included in FIG. 1 have the same reference numerals. In place of the temperature sensor 17 located downstream of the catalytic converter 5 in the embodiment of FIG. 1, a temperature sensor 19 providing a signal on the line 15 is located inside the catalytic converter, preferably at approximately one-third of the axial length of the catalytic converter downstream from the entrance, so that it quickly detects temperature increases caused by spark failure. In addition, a second fuel injection nozzle 8′, actuated through a line 12′, is disposed between the catalytic converter and the engine to provide additional unburned fuel to the catalytic converter, if necessary. In the control unit 9, a difference circuit 20, a differentiation circuit 21 and a memory unit 22 are arranged to receive signals from the sensors 18 and 19. The differentiation and storage of the value thus obtained, which is proportional to the conversion ratio, is thus possible, even though deceleration conditions are normally too short to provide signals which can be evaluated to provide a conversion ratio. A signal output transmitter is connected to the memory unit 22 to provide for comparison of conversion ratios over time.

In accordance with the invention, a method and an apparatus for its execution have thus been provided which assure monitoring of the conversion ratio of a catalytic converter with little effort.

Although the invention has been described herein with reference to specific embodiments, many modifications and variations herein will readily occur to those skilled in the art. Accordingly, all such variations and modifications are included within the intended scope of the invention.

I claim:

1. A method for monitoring the conversion ratio of a catalytic converter disposed in the exhaust gas system of an internal combustion engine having spark ignition comprising causing at least one ignition suppression during a deceleration phase of operation of the internal combustion engine to cause a defined amount of unburned fuel-air mixture to be supplied to the catalytic converter, and comparing temperature values of the exhaust gases at spaced locations assuming different temperature values due to chemical reaction of said fuel-air mixture in the catalytic converter to provide a monitoring signal.

2. A method according to claim 1 wherein temperature values at locations upstream and downstream of the catalytic converter are compared.

3. A method according to claim 1 wherein the monitoring signal is produced only after the catalytic converter has reached its starting temperature even in an aged stage.

4. A method according to claim 1 wherein the monitoring signal is generated after each startup of the internal combustion engine.

5. A method according to claim 1 wherein the monitoring signal is generated at selected time intervals.

6. A method according to claim 1 including storing the monitoring signal.

7. Apparatus for monitoring the conversion ratio of a catalytic converter receiving exhaust gases from a spark-ignited internal combustion engine comprising control means for causing ignition suppression, fuel mixture control means for controlling the supply of preset quantities of fuel and air to the engine including switch means for signalling a deceleration operation of the internal combustion engine, and temperature sensor means for detecting temperature conditions at spaced locations assuming different temperature values due to chemical reaction of said fuel-air mixture in the catalytic converter.

8. Apparatus according to claim 7 wherein the switch means is a throttle flap switch for supplying an activation signal to the control means when the throttle flap is in the closed position.

9. Apparatus according to claim 7 including a throttle flap and bypass means for bypassing the throttle flap, and valve means in the bypass means responsive to the control means for controlling the quantity of air supplied to the internal combustion engine.

10. Apparatus according to claim 7 wherein the fuel mixture control means includes fuel injection nozzle means disposed downstream of a throttle flap in the air supply to the internal combustion engine.

11. Apparatus according to claim 10 wherein a fuel injection nozzle means is disposed between the catalytic converter and the internal combustion engine.

12. Apparatus according to claim 7 wherein the temperature sensor means is disposed upstream and downstream with respect to the flow of exhaust gases through the catalytic converter, and control means including difference signal means, signal differentiating means and signal memory means.

13. Apparatus according to claim 12 including temperature sensor means disposed in the upstream half of the catalytic converter to which exhaust gases are supplied.

* * * * *

UNITED STATES PATENT AND TRADEMARK OFFICE
CERTIFICATE OF CORRECTION

PATENT NO. : 5,133,184
DATED : July 28, 1992
INVENTOR(S) : Istvan Geiger

It is certified that error appears in the above-identified patent and that said Letters Patent is hereby corrected as shown below:

Title page: <u>Item 30</u>, add the following:
--Jan. 9, 1991   Fed. Rep. of Germany ........4100397--;

<u>Column 1, line 28</u>, "the patent" should read --that patent--;

<u>Column 2, line 57</u>, "need to" should read --need not--;

<u>Column 3, lines 5-6</u>, "a rmp siganl" should read --an rpm signal--.

Signed and Sealed this

Fourteenth Day of September, 1993

Attest:

BRUCE LEHMAN

Attesting Officer

Commissioner of Patents and Trademarks